United States Patent
Juliato

(10) Patent No.: US 10,782,790 B2
(45) Date of Patent: Sep. 22, 2020

(54) SYSTEM AND METHOD TO COLLECT GESTURE INPUT THROUGH WRIST TENDON AND MUSCLE SENSING

(71) Applicant: Intel Corporation, Santa Clara, CA (US)

(72) Inventor: Marcio Juliato, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 15/774,932

(22) PCT Filed: Dec. 22, 2015

(86) PCT No.: PCT/US2015/067534
§ 371 (c)(1),
(2) Date: May 9, 2018

(87) PCT Pub. No.: WO2017/111972
PCT Pub. Date: Jun. 29, 2017

(65) Prior Publication Data
US 2018/0348880 A1 Dec. 6, 2018

(51) Int. Cl.
| | |
|---|---|
| G06F 3/01 | (2006.01) |
| A61B 5/11 | (2006.01) |
| A61B 5/00 | (2006.01) |
| G04G 21/02 | (2010.01) |
| G04C 3/00 | (2006.01) |
| G06F 1/16 | (2006.01) |

(52) U.S. Cl.
CPC .............. G06F 3/017 (2013.01); A61B 5/002 (2013.01); A61B 5/1107 (2013.01);
(Continued)

(58) Field of Classification Search
CPC .......... G06F 3/017; G06F 3/015; G06F 3/014; G06F 1/163; G04C 3/002; G04G 21/025;
(Continued)

(56) References Cited

U.S. PATENT DOCUMENTS

| | | | |
|---|---|---|---|
| 2004/0254617 A1* | 12/2004 | Hemmerling | ......... A61B 7/006 607/48 |
| 2005/0206613 A1* | 9/2005 | Chan | ..................... G06F 1/3203 345/156 |

(Continued)

FOREIGN PATENT DOCUMENTS

| | | |
|---|---|---|
| WO | 2015060856 | 4/2015 |
| WO | 2017111972 | 6/2017 |

OTHER PUBLICATIONS

International Searching Authority, "International Preliminary Report on Patentability," issued in connection with application No. PCT/US2015/067534, dated Jun. 26, 2018, 8 pages.
(Continued)

*Primary Examiner* — Liliana Cerullo
(74) *Attorney, Agent, or Firm* — Hanley, Flight & Zimmerman, LLC

(57) ABSTRACT

A system and method to collect gesture input through wrist tendon and muscle sensing are disclosed. A particular embodiment includes: a sensor array integrated into a wristband, the sensor array including a plurality of pressure sensors positioned for contact with particular locations on a wrist of a user wearing the wristband; and a controller unit, the controller unit including a communication interface, the controller unit being configured to: receive a plurality of sensor signals generated by the sensor array, the plurality of sensor signals corresponding to movement detected at particular locations on the wrist of the user; convert the plurality of sensor signals to a digital representation; generate a composite data packet by combining the plurality of converted sensor signals into a composite digital value; and provide the composite digital value to a processing unit of a wearable device for use in control of a user interface in the wearable device.

19 Claims, 16 Drawing Sheets

(52) U.S. Cl.
CPC .......... *A61B 5/1114* (2013.01); *A61B 5/4519* (2013.01); *A61B 5/681* (2013.01); *G04C 3/002* (2013.01); *G04G 21/025* (2013.01); *G06F 1/163* (2013.01); *G06F 3/014* (2013.01); *G06F 3/015* (2013.01); *A61B 2562/0247* (2013.01); *A61B 2562/043* (2013.01)

(58) Field of Classification Search
CPC ..... A61B 5/681; A61B 5/1107; A61B 5/1114; A61B 5/002; A61B 5/4519; A61B 5/4523; A61B 2562/043; A61B 2562/0247
See application file for complete search history.

(56) References Cited

U.S. PATENT DOCUMENTS

| | | | |
|---|---|---|---|
| 2007/0208262 A1* | 9/2007 | Kovacs | ............... A61B 5/0404 600/509 |
| 2010/0152619 A1* | 6/2010 | Kalpaxis | .............. A61B 5/0002 600/592 |
| 2012/0188158 A1 | 7/2012 | Tan et al. | |
| 2013/0265229 A1 | 10/2013 | Forutanpour et al. | |
| 2015/0084860 A1* | 3/2015 | Aleem | ................... G06F 3/017 345/156 |
| 2015/0301606 A1 | 10/2015 | Andrei | |
| 2015/0309582 A1 | 10/2015 | Gupta | |
| 2016/0062320 A1* | 3/2016 | Chung | ................... G04G 21/00 368/282 |

OTHER PUBLICATIONS

International Searching Authority, "International Search Report and Written Opinion," issued in connection with International Patent Application No. PCT/US2015/067534, dated Sep. 21, 2016, 9 pages.

* cited by examiner

Table 1: Sensor location and associated color code

| Sensor | Color | Wrist Location |
|---|---|---|
| T0 | | Top Edge Left |
| T1 | | Top Far Left |
| T2 | | Top Mid Left |
| T3 | | Top Center Left |
| T4 | | Top Center Right |
| T5 | | Top Mid Right |
| T6 | | Top Far Right |
| T7 | | Top Edge Right |

| Sensor | Color | Wrist Location |
|---|---|---|
| B0 | | Bottom Edge Left |
| B1 | | Bottom Far Left |
| B2 | | Bottom Mid Left |
| B3 | | Bottom Center Left |
| B4 | | Bottom Center Right |
| B5 | | Bottom Mid Right |
| B6 | | Bottom Far Right |
| B7 | | Bottom Edge Right |

Fig. 2

Serial package formed by sixteen bytes

Waveforms Corresponding to Several Finger Positions

Logic for Collecting and Processing Wrist Sensor Data
-1100-

Provide a sensor array integrated into a wristband, the sensor array including a plurality of pressure sensors positioned for contact with particular locations on a wrist of a user wearing the wristband.
-1110-

Provide a controller unit, the controller unit including a communication interface.
-1120-

Receive a plurality of sensor signals generated by the sensor array, the plurality of sensor signals corresponding to movement detected at particular locations on the wrist of the user.
-1130-

Convert the plurality of sensor signals to a digital representation.
-1140-

Generate a composite data packet by combining the plurality of converted sensor signals into a composite digital value.
-1150-

Provide the composite digital value to a processing unit of a wearable device for use in control of a user interface in the wearable device.
-1160-

Fig. 15    End

SYSTEM AND METHOD TO COLLECT GESTURE INPUT THROUGH WRIST TENDON AND MUSCLE SENSING

TECHNICAL FIELD

This patent application relates to electronic systems, mobile devices, wearable devices, Internet of Things (IoT) devices, data sensing systems, human/machine interfaces, gesture sensing, and computer-implemented software, according to various example embodiments, and more specifically to a system and method to collect gesture input through wrist tendon and muscle sensing.

BACKGROUND

Smart watches, such as the devices commercialized by Samsung® and Apple®, are receiving increasing attention and becoming more popular. Given the wearable nature of those devices, their form factor is very limited. As a result, these wearable devices have relatively small display screen space to present information to the user. Similar to cellphones, designers typically use a liquid-crystal display (LCD) to present information to the user, which is also used as a touch screen device for user input. The small display screen size on smart watches requires users to cope with very small font sizes, tiny application (app) icons, and difficult to use menus. Additionally, smart watches usually need to provide side buttons or wheels on the device to provide extra interactive user interfaces. In most smart watch use cases, the user wears the watch on one of their wrists and uses the opposite hand to operate the device while staring at its display screen. Unfortunately, this keeps both hands busy and requires special attention from the user to get the intended results from using the aforementioned limited interface. Texting while driving has been a serious issue, which may eventually get worse as smart watches incorporate more functionalities and become more popular. The limited smart watch user interface only serves to exacerbate the problem of distracted driving.

Conventional systems provide a wrist band that conforms to a wrist of a user. The wrist band provides a user input system that includes a motion tracking sensor that tracks aerial motion of the wrist of the user as aerial motion data. Other conventional systems use a forearm band to measure the electromyography, or EMG, of the forearm muscles. EMG involves testing the electrical stimulation of muscles. Still other conventional systems use a camera to track body movement. However in these existing systems, a separate band or device is required to be attached to the body of the user or used with the system so the system can detect arm movement for input control. It is inconvenient, redundant, and expensive to wear or carry additional devices for user input control.

BRIEF DESCRIPTION OF THE DRAWINGS

The various embodiments are illustrated by way of example, and not by way of limitation, in the figures of the accompanying drawings in which:

FIG. 2 illustrates the colors and labels assigned to each of the pressure sensors in the sensor array to make it easier to quickly reference a particular sensor in an example embodiment;

FIG. 15 is a processing flow chart illustrating an example embodiment of a method as described herein.

DETAILED DESCRIPTION

In the following description, for purposes of explanation, numerous specific details are set forth in order to provide a thorough understanding of the various embodiments. It will be evident, however, to one of ordinary skill in the art that the various embodiments may be practiced without these specific details.

In the various embodiments described herein, a system and method to collect gesture input through wrist tendon and muscle sensing are disclosed. Example embodiments are described wherein hand and wrist movements are used to interact with smart watches or other wearable devices. The example embodiments described herein integrate a hand/wrist user input capability with a standard smart watch or other wearable, thereby eliminating the need for additional devices and eliminating the need for the user to utilize both hands to operate the device. In addition to the usual touch screen and side buttons/wheels on the standard smart watch, the user can now utilize hand/wrist gestures to perform actions on the smart watch. In various example embodiments described herein, a hand/wrist user input capability can be integrated into the internal surface of a smart watch or wearable device wristband. As a result, gesture control can be achieved with inexpensive components and embedded in the smart watch or wearable device wristband itself, thereby avoiding cameras, extra bands on the user's arm, or other required devices. Gesture control can be very helpful while dealing with tiny display screens of wearable devices. In fact, gesture control may eventually become the preferred method to interface with smart watches or other wearable devices.

In contrast to conventional implementations, the various example embodiments described herein relate to muscle and tendon sensing on the wrist, not on the forearm. The various example embodiments also do not use electromyography or cameras for gesture sensing. Instead, the various example embodiments use inexpensive pressure sensors that can readily incorporated onto the internal surface of a smart watch or wearable device wristband.

In various example embodiments, sensors and control logic, integrated into the wristband of a smart watch or wearable device, are provided to analyze the static and dynamic positions of the wrist tendons and muscles. In the wrist or arm of a human body, there are two types of tendons: flexors and extensors. An example embodiment uses pressure sensors mounted around the inside surface of a wristband to detect the relative position and movement of those tendons. Pressure detecting sensors are provided on the posterior and anterior sides of the wrist. The wristband is configured to achieve a minimum mounting pressure to ensure that the sensors are in close contact with the surface of the wrist. The details of various example embodiments are provided below in connection with the accompanying figures.

Figure 1:
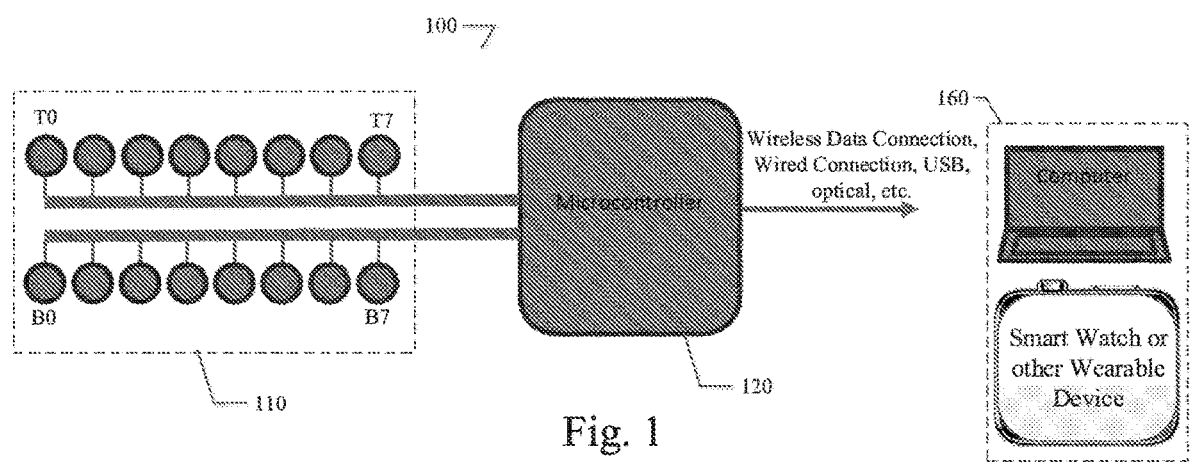
FIG. 1 is a block diagram of a system and apparatus for hand/wrist gesture input integrated with a standard smart watch or other wearable wristband according to an example embodiment.

Turning now to FIG. 1, a block diagram illustrates a system and apparatus 100 for hand/wrist gesture input integrated with a standard smart watch or other wearable device wristband according to an example embodiment. In the example embodiment, sixteen force resistive sensors or pressure sensors in a sensor array 110 can be used to sense the movement, contraction, or extension of tendons or muscles on the posterior and anterior sides of a wrist of a user. In the example embodiment, each sensor can be a force resistive sensor (e.g., FSR400), which is fed with five volts (5V) of electrical power. It will be apparent to those of ordinary skill in the art in view of the disclosure herein that a greater or fewer quantity of sensors in sensor array 110 can be used in a particular embodiment. In the example embodiment, half of the sensors in the sensor array 110 can be positioned on the posterior side (top or T) of the user's wrist. Each sensor on the posterior side of the wrist can be labeled with the designation T0 through T7. As described in more detail below, these designations for each of the sensors in the sensor array 110 can correspond to a particular position in a data object or data packet created from the data provided by the sensor array 110. The other half of the sensors in the sensor array 110 can be positioned on the anterior side (bottom or B) of the user's wrist. Each sensor on the anterior side of the wrist can be labeled with the designation B0 through B7. As described in more detail below, the sensor array 110 can be integrated with a wristband and configured to make contact with the user's wrist at particular locations to detect the relative position and movement of the user's wrist tendons and muscles.

Referring still to FIG. 1, a block diagram illustrates a microcontroller 120 in data communication with the sensor array 110. In the example embodiment, the microcontroller 120 can be a semiconductor microprocessor, integrated circuit, application specific integrated circuit (ASIC), programmable logic device (PLD), digital signal processor (DSP), field programmable gate array (FPGA), discrete logic component, an Arduino™ Mega board (Atmel™ microcontroller), or other controller, data processor, or signal processor system fabricated using conventional technology. As shown in FIG. 1, the sensor array 110 can be electrically connected or wirelessly connected to the microcontroller 120. Each sensor in the sensor array 110 can generate a sensor signal corresponding to a level of force or pressure applied to the sensor. The output signal from each sensor can be electrically transferred to the microcontroller 120 as an analog sensor signal through a pull down resistor (e.g., a 10*k* ohms resistor). Thus, the analog sensor signal received by the microcontroller 120 from each sensor in the sensor array 110 can be configured to vary linearly from a "no pressure" value (e.g., 0V) when no pressure is applied to the sensor to a "maximum pressure" value (e.g., 5V) when maximum pressure is applied to the sensor. In the example embodiment, the microcontroller 120 is configured to receive the sixteen analog sensor signals from the sensor array 110 and to convert the analog sensor signals to a digital representation via an internal analog-to-digital (A/D) converter. As a result, the microcontroller 120 can produce digital sensor signals with digital values representing the level of force or pressure applied to each sensor. In a particular embodiment, the microcontroller 120 can convert the analog sensor signals to digital sensor signals and forward the digital sensor signals in a formatted binary format to an integrated or separate computing device 160 via a wired or wireless data connection. The computing device 160 can be a computer, tablet, or wearable device, such as a smart watch. The integrated or separate computing device 160 can thereby receive the digital sensor signals corresponding to the force or pressure detected by the sensor array 110. In an embodiment, the digital sensor signals can also be forwarded in a formatted binary format to a control logic or data processing component configured to manage a user interface based on the pressure detected by the sensor array 110, which corresponds to movement of the user's wrist tendons or muscles. In an example embodiment, the control logic used in the microcontroller 120 to process the digital sensor signals can be integrated with the control logic or data processing component as provided in the integrated or separate computing device 160. As such, the function of the microcontroller 120 can also be integrated into the processing elements of a wearable device, such as a smart watch and used to control a user interface in the wearable device.

FIG. 2 illustrates the colors and labels assigned to each of the pressure sensors in the sensor array 110 in the example embodiment to make it easier to quickly reference a particular sensor in the array. The labels assigned to each of the pressure sensors in the sensor array 110 can also correspond to the arm or wrist position where the sensor is located and the associated digital sensor signals corresponding to the force or pressure detected by each of the sensors in the sensor array 110 at the corresponding arm or wrist position. As shown in FIG. 2, each of the sensors in the sensor array 110 are positioned at a different point on the wrist of the user. As described above, half of the sensors (T0 through T7) in the sensor array 110 are positioned on the posterior (top) side of the user's wrist. The other half of the sensors (B0 through B7) are positioned on the anterior (bottom) side of the user's wrist. The sensor labels T0-T7 and B0-B7 also correspond to the force or pressure detected by each of the sensors at the corresponding arm or wrist position. As described in more detail below, these digital sensor signals (T0-T7 and B0-B7) can be combined to form a composite digital value or data packet corresponding to the sensor signature detected by the sensor array 110 at a particular point in time.

Figure 3:
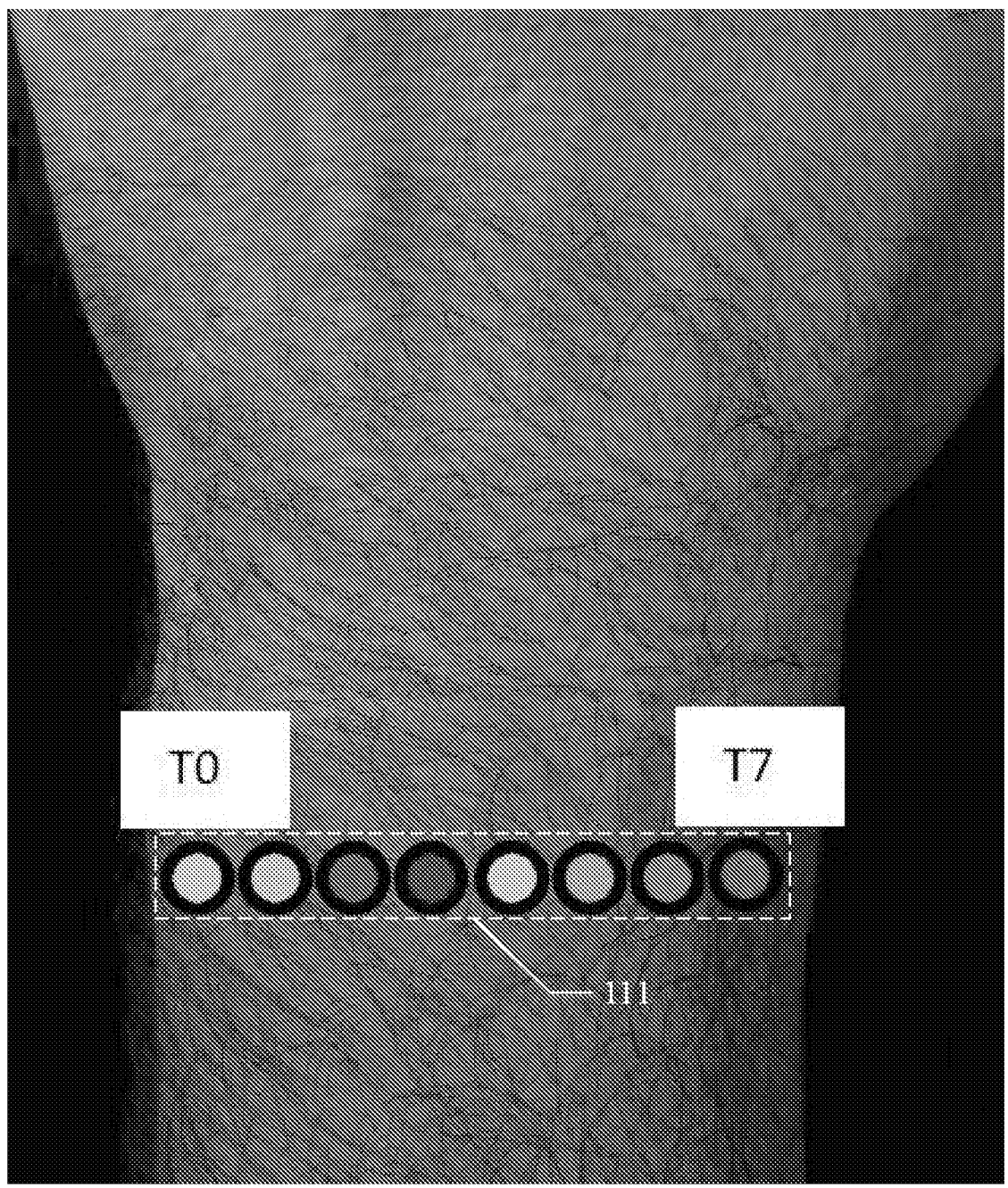
FIG. 3 illustrates an example embodiment of the placement of the pressure sensors in the sensor array on the posterior side of the wrist of a user.
Figure 4:
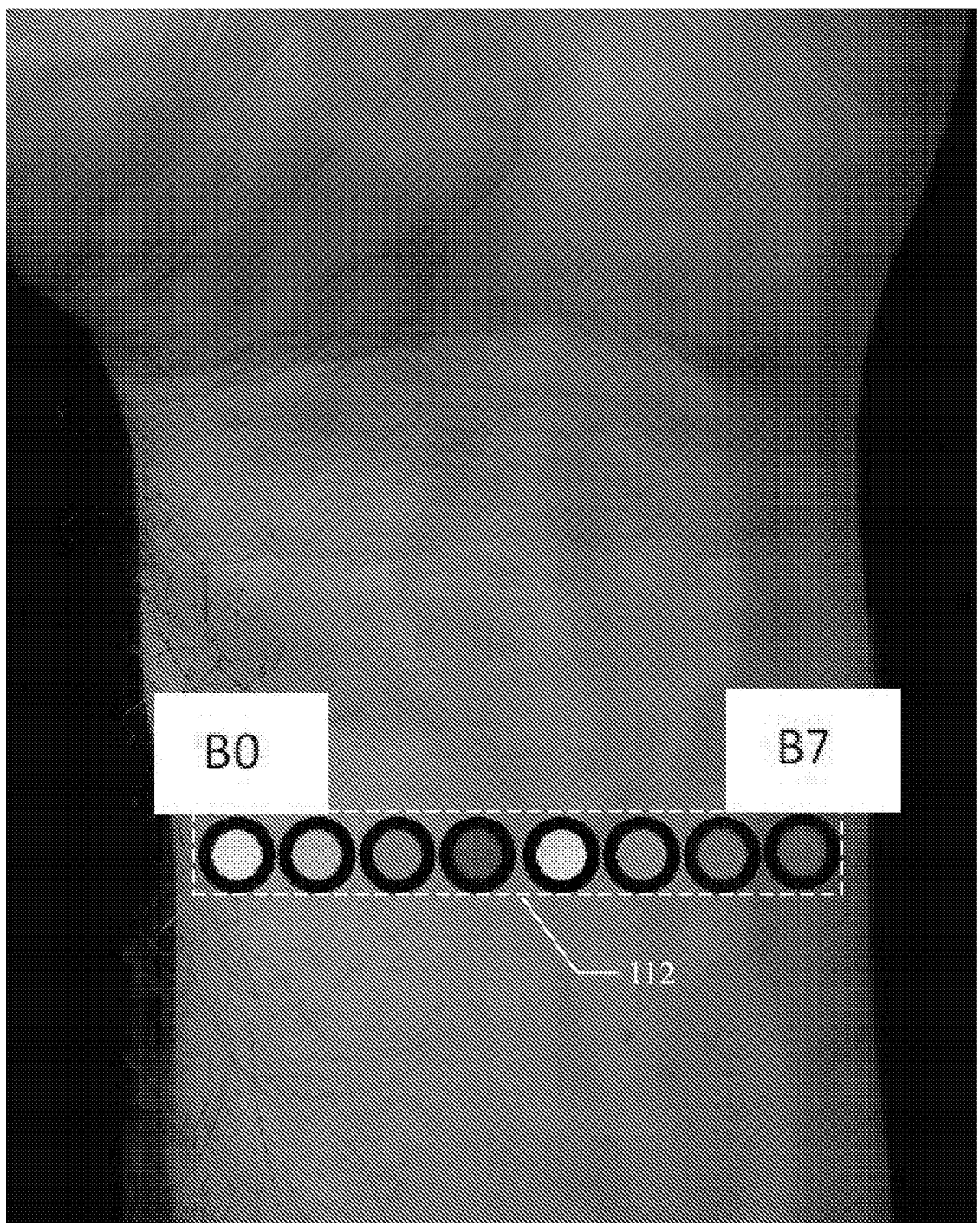
FIG. 4 illustrates an example embodiment of the placement of the pressure sensors in the sensor array on the anterior side of the wrist of a user.

FIG. 3 illustrates an example embodiment of the placement of the pressure sensors 111 in the sensor array 110 on the posterior side of the wrist of a user. FIG. 4 illustrates an example embodiment of the placement of the pressure sensors 112 in the sensor array 110 on the anterior side of the wrist of a user. As shown, the placement of the sensors 111/112 on the posterior and anterior sides of the wrist can be configured to correspond to the locations of tendons and muscles in the wrist of the user. These tendons and muscles move, flex, contract, or extend when the wrist, fingers, or thumb are moved in a particular manner. These movements can be detected by the sensor array 110 and the sensors 111/112 on the posterior and anterior sides of the wrist. As shown in FIG. 3, the sensors 111 can produce digital sensor signals T0 through T7, which correspond to the pressure levels detected at particular points on the posterior side of the wrist of the user. As shown in FIG. 4, the sensors 112 can produce digital sensor signals B0 through B7, which correspond to the pressure levels detected at particular points on the anterior side of the wrist of the user. These sensor signals can correspond to particular gestures made by the user while wearing a wristband with the sensor array 110 embedded therein.

Figure 5:
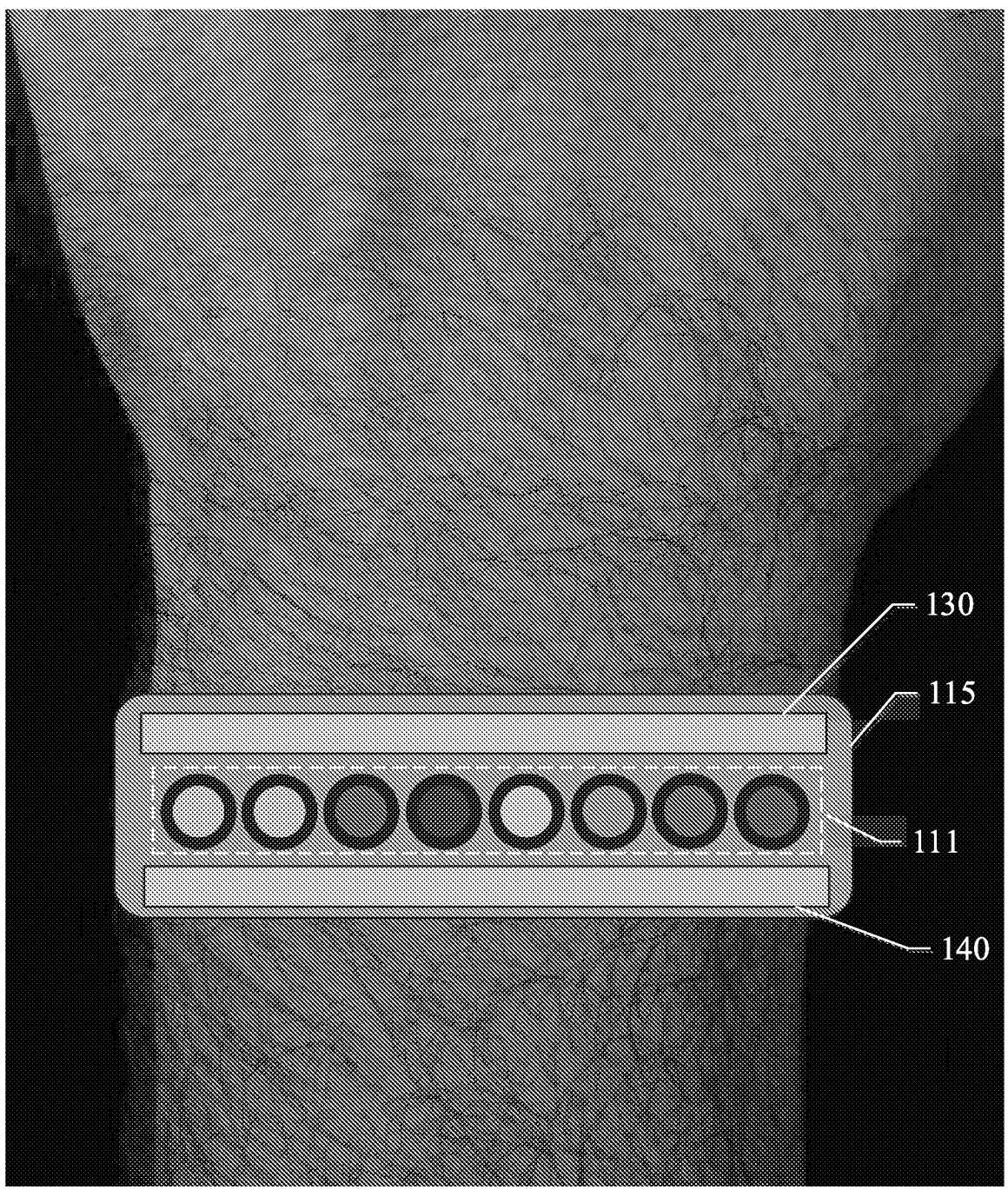
FIG. 5 illustrates an example embodiment of the integration of the sensor array with the wristband on the posterior side of the wrist of a user.
Figure 6:
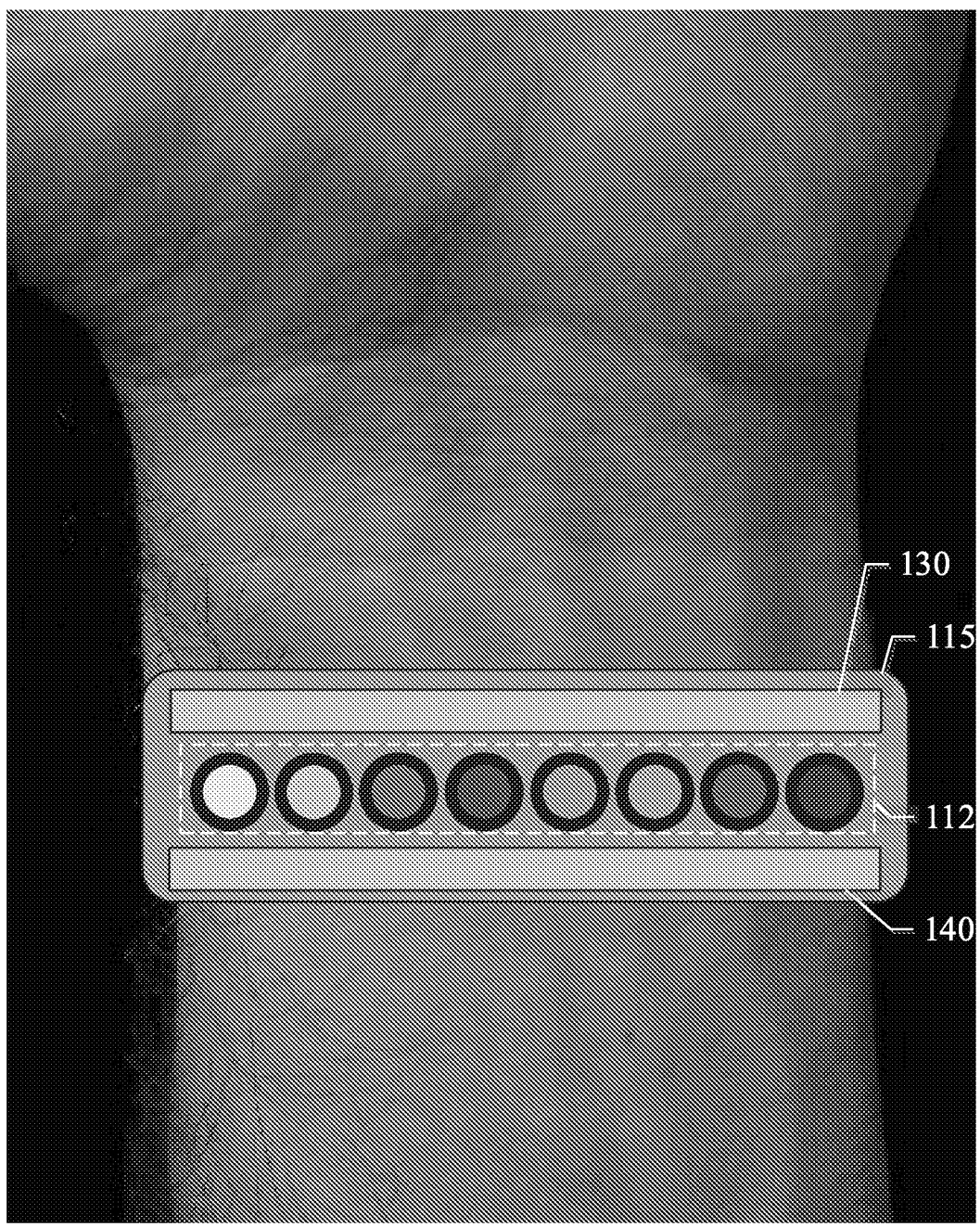
FIG. 6 illustrates an example embodiment of the integration of the sensor array with the wristband on the anterior side of the wrist of a user.

FIG. 5 illustrates an example embodiment of the integration of the sensor array 110 with the wristband 115 on the posterior side of the wrist of a user. FIG. 6 illustrates an example embodiment of the integration of the sensor array 110 with the wristband 115 on the anterior side of the wrist of a user. As such, the sensor array 110 can be integrated or embedded into a wristband 115 to be worn on the wrist of a user. The wristband 115 can be fabricated from any of a variety of materials including plastic, rubber, silicone, bonded polymer, polyurethane, leather, metal, or other materials. The sensor array 110 can be integrated into the wristband 115 during manufacture using conventional techniques. As described above, the sensor array 110 and the sensors 111/112 can be integrated into the wristband 115 to correspond to the particular positions of tendons and muscles on the posterior and anterior sides of the wrist of a user. The wristband 115 of an example embodiment can be configured to include a data unit 130 and power and communication unit 140 of controller unit 120. The data unit 130 and power and communication unit 140 of an example embodiment are described in more detail below.

Figure 7:
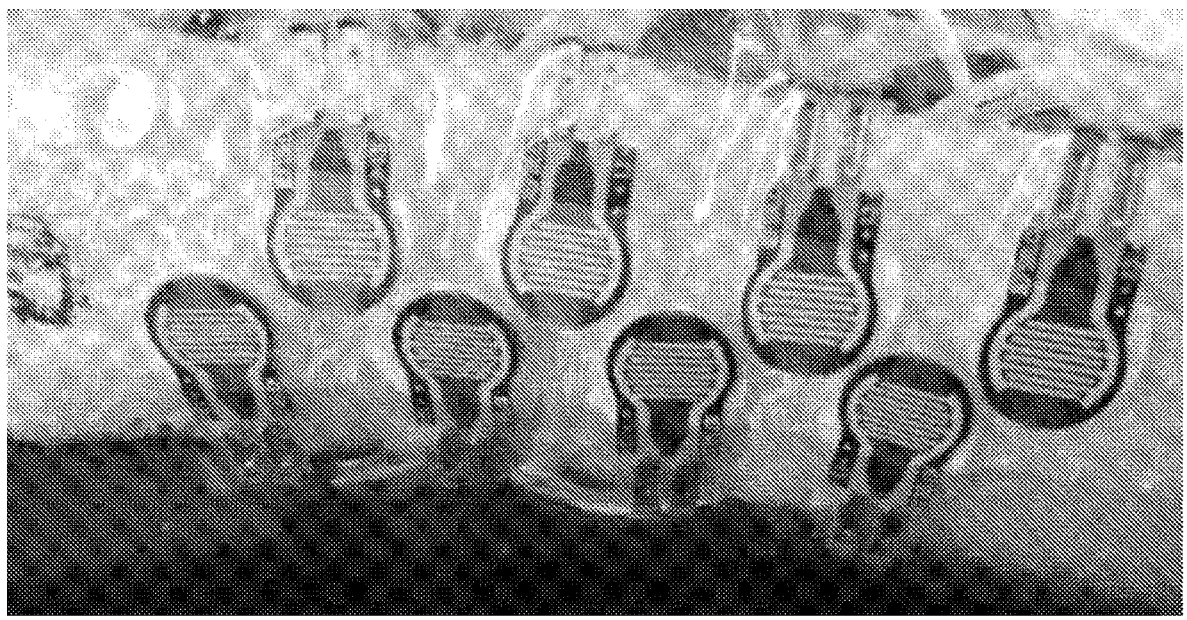
FIG. 7 illustrates an example embodiment of a portion of the sensor array.

FIG. 7 illustrates an example embodiment of a portion of the sensor array 110. In an example embodiment, the sensors of the sensor array 110 should be in close contact with the wrist to improve the detection of movement of the wrist tendons and muscles. In various embodiments, a particular type of sensor with a desired level of sensitivity can be used to provide the tendon/muscle detection needed given the contact provided by a particular wristband 115. In example embodiments, the sensors used, as described above, were chosen based on their relatively low price and satisfactory level of performance In an alternative embodiment, a Velcro™ brand wristband can be used to keep the wristband 115 tight to the wrist. In another alternative embodiment, an anti-static foam can be used to accommodate the shape of the wrist. The use of an anti-static foam can provide some cushioning that facilitates the ability of the sensor array 110 to conform to the round shape of the wrist while keeping the sensor array 110 tightly coupled with the skin. In each of these configurations of the example embodiments, the sensor array 110 can be in contact with the wrist of the user and configured to detect movement as the wrist tendons/muscles move.

Figure 8:
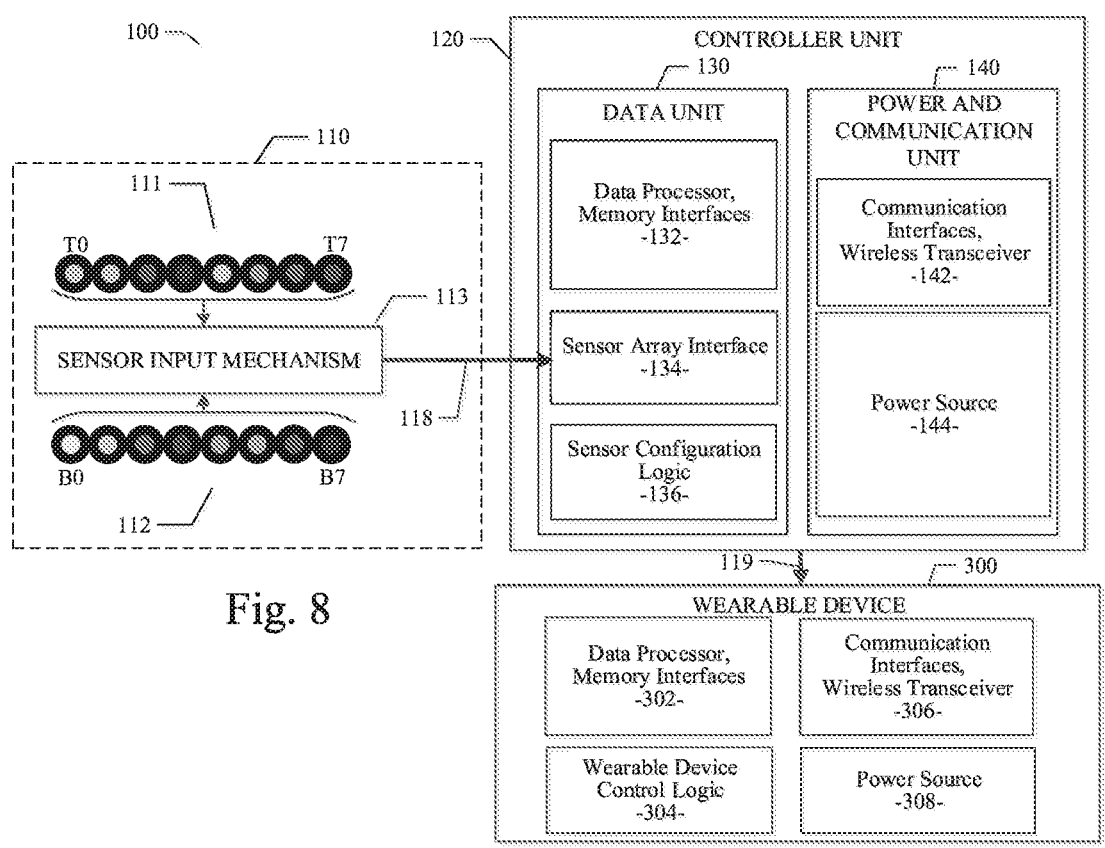
FIG. 8 is a block diagram of a system and apparatus for hand/wrist gesture input integrated with the wristband of a standard smart watch or other wearable device according to an example embodiment.

FIG. 8 is a block diagram of a system and apparatus 100 for hand/wrist gesture input integrated with the wristband of a standard smart watch or other wearable device according to an example embodiment. In the embodiment shown, the sensor array 110 is in data communication with the controller unit 120. As described above in regard to an example embodiment, both the sensor array 110 and the controller unit 120 can be integrated into the wristband 115 to detect movement in the tendons and muscles in the wrist of the user. In another example embodiment (e.g., see FIG. 9), the controller unit 120 can be integrated into the smart watch or other wearable device and the sensor array 110 can be integrated into the wristband 115. The sensor array 110 can be in data communication with the controller unit 120 via a data connection 118. In the embodiment shown in FIG. 8, the controller unit 120 can be in data communication with the wearable device 300 via a data connection 119, which can be a wireless or wired data connection.

The sensor array 110 of an example embodiment can include a first sensor array portion 111 to detect movement or pressure changes on the posterior side of the wrist of the user. The sensor array 110 of an example embodiment can also include a second sensor array portion 112 to detect movement or pressure changes on the anterior side of the wrist of the user. The sensor input mechanism 113 is provided to collect the analog sensor signals from each of the plurality of sensors of sensor array 110 and to provide the analog sensor signals to a sensor array interface 134 of a data unit 130 of the controller 120. The sensor input mechanism 113 can provide the plurality of sensor inputs on a periodic or continuous basis. The sensor input mechanism 113 can provide the plurality of sensor inputs on a serial interface using standard time-division multiplexing techniques or as a plurality of parallel signals. In an alternative embodiment, the sensor input mechanism 113 can include an analog-to-digital converter to convert the analog sensor signals to a digital representation and to provide the digital sensor signals to the sensor array interface 134.

In the example embodiment shown in FIG. 8, the controller unit 120 can be configured to include a data unit 130 and a power and communication unit 140. The data unit 130 of an example embodiment can include the sensor array interface 134, a data processor and memory interface component 132 (herein processing module 132), and a sensor array configuration logic component 136. As described above, the sensor array interface 134 is configured to receive the plurality of sensor inputs from the sensor array 110. In an example embodiment, the sensor inputs can be received as a plurality of analog sensor signals at the sensor array interface 134. The processing module 132 can include an analog-to-digital converter to convert the received plurality of analog sensor signals to a digital representation and a corresponding plurality of digital sensor signals. In an example embodiment, each analog sensor signal can be converted to a digital form represented as an 8-bit digital value. It will be apparent to those of ordinary skill in the art in view of the disclosure herein that a different quantity of bits can be used in an alternative embodiment to represent each sensor value. The processing module 132 can store the plurality of digital sensor signal values in an internal memory device. In the example embodiment, the processing module 132 can also aggregate or integrate the plurality of digital sensor signal values into a composite data packet representation of the current state of each of the sensors in the sensor array 110. An example of this data packet representation is shown in FIG. 10.

Figure 10:
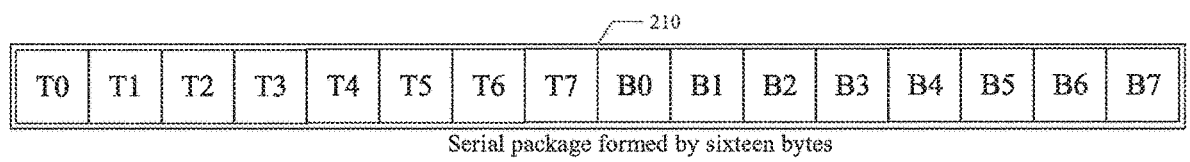
FIG. 10 illustrates an example embodiment of a sample data packet formed with sixteen 8-bit digital readings from the sensors in the sensor array.

FIG. 10 illustrates an example embodiment of a sample data packet 210 formed with sixteen 8-bit digital readings from the sensors in the sensor array 110. On a periodic basis, the processing module 132 can sweep through each analog input of the plurality of sensors in the sensor array 110 and convert the analog sensor signals into a digital form. As described above, the plurality of digital sensor signal values can be stored in an internal memory device. Additionally, the processing module 132 can combine each of the individual 8-bit digital sensor values from each sensor into a composite data packet, such as the sample data packet 210 shown in FIG. 10. The composite data packet 210 can represent the state of the sensor array 110 at a particular point in time. In the example embodiment, one half of the composite data packet 210 can represent the state of the posterior sensors 111 and the other half of the composite data packet 210 can represent the state of the anterior sensors 112. It will be apparent to those of ordinary skill in the art in view of the disclosure herein that a different arrangement of the data elements of the composite data packet 210 can be used in an alternative embodiment to represent the state of the sensor array 110. The generation of the composite data packet 210 provides a convenient and efficient data representation to transfer the sensor data to other external processing devices via the communication interfaces provided by the processing module 132. For example, the composite data packet 210 with sixteen 8-bit digital sensor readings can be transferred to an internal processing element or external device, such as a wearable device, through a variety of wired or wireless interfaces, including serial interfaces, USB, and wireless protocols.

Referring again to FIG. 8, the data unit 130 is shown to include a sensor configuration logic module 136. The sensor configuration logic module 136 includes logic or instructions executable by the processing module 132 to calibrate, initialize, and configure the sensors in the sensor array 110. For example, the sensor configuration logic module 136 can prompt a user to make a series of gestures while wearing an embodiment of the apparatus as described herein. The sensor configuration logic module 136 can record the signature of the signals from the sensor array 110 as each gesture is made. These signatures can be used to correlate the sensor data from the sensor array 110 with the specific user inputs provided by a user. Additionally, the sensor configuration logic module 136 can be used to adjust the sensitivity of each of the sensors in the sensor array 110.

Referring still to FIG. 8, the controller 120 is shown to include a power and communication unit 140. As described above, the wristband 115 of an example embodiment can be configured to include a sensor array 120 and the data unit 130. The power and communication unit 140 is used to provide stored electrical power for the sensor array 120 and the data unit 130. The power and communication unit 140 can also be combined with the controller unit 120 and integrated into the wristband 115. The power and communication unit 140 can include a power source 144, which can be a source of stored electrical or a portable power supply (e.g., a battery), a source of generated electrical power (e.g., a solar cell array, a motion generator, energy harvesting, etc.), or other type of electrical power source. The power and communication unit 140 can also include a communication interface component and/or a wireless transceiver 142 powered by the power source 144, to enable the controller 120 to wirelessly or via a wired data interface transfer data to an external device, such as a smart watch, wearable device, or the like. In this manner, the controller 120 can transfer the composite data packet 210 representing the state of the sensor array 110 to an external device for use by a user interface controller in the external device, such as a smart watch, wearable device, or the like. As a result, the data corresponding to the particular gestures made by a user while wearing the apparatus as described herein can be wirelessly transferred to a user interface of an external device, thereby enabling the apparatus as described herein to wirelessly or via a wired data interface control the user interface of the external device, such as a smart watch, wearable device, or the like.

Figure 9:
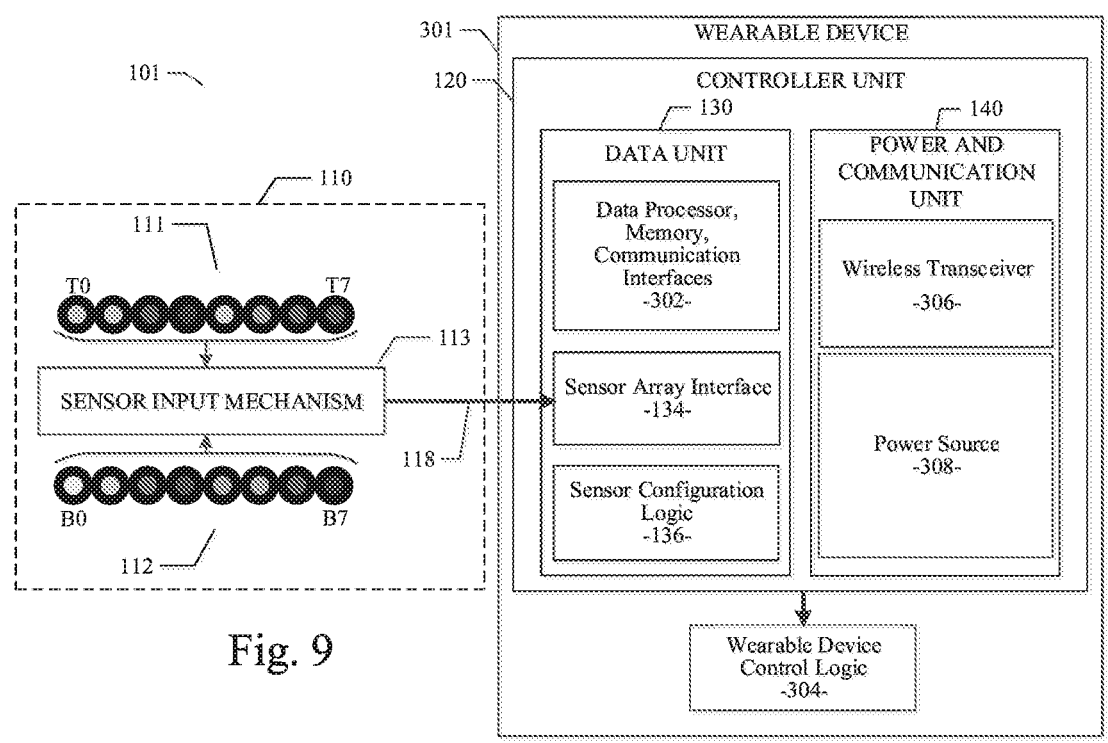
FIG. 9 is a block diagram of a system and apparatus for hand/wrist gesture input integrated with the wristband of a standard smart watch or other wearable device wherein the controller unit is integrated into the smart watch or other wearable device according to an example embodiment.

FIG. 9 is a block diagram of a system and apparatus for hand/wrist gesture input integrated with the wristband of a standard smart watch or other wearable device wherein the controller unit is integrated into the smart watch or other wearable device 301 according to an example embodiment. In the example embodiment shown in FIG. 9, the function of controller unit 120, as described above, can be integrated into the wearable device 301. A data processor 302 in the wearable device 301 can be used to execute the control logic to manage the data received from the sensor array 110. The wireless transceiver 306 in the wearable device 301 can be used to wirelessly transmit the data to other devices. The power source 308 in the wearable device 301 can be used to power the system components. The function of the wearable device itself, including user interface logic for the wearable device 301, can be performed by the wearable device control logic 304. In this manner, the controller 120, as integrated into the wearable device 301, can transfer the composite data packet 210 representing the state of the sensor array 110 to the user interface logic of the wearable device 301 in the wearable device control logic 304. As a result, the data corresponding to the particular gestures made by a user while wearing the apparatus as described herein can be transferred to the user interface of the wearable device, thereby enabling the apparatus as described herein to control the user interface of the device, such as a smart watch, wearable device, or the like.

Figure 11:
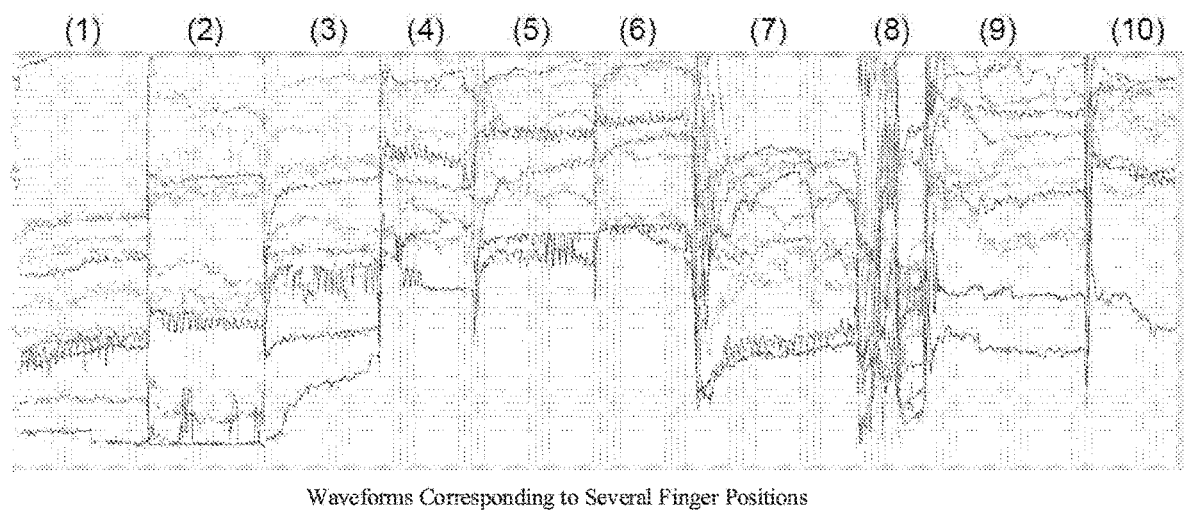
FIG. 11 illustrates an example embodiment of sample waveforms corresponding to several finger positions as read from the sensor array.

FIG. 11 illustrates an example embodiment of sample waveforms corresponding to several finger positions as read from the sensor array 110. In the example embodiment, the vertical axis corresponds to the sensor data values read from each of the sensors in the sensor array 120. In the example embodiment, each sensor reading may vary from 0 to 255 decimal, each of which are plotted in the vertical axis. The horizontal axis shows all readings over time.

As shown in FIG. 11, ten different sample gestures are made with the corresponding sensor data signatures shown in FIG. 11 in ten corresponding columns labeled (1) through (10). The ten different sample gestures are described below:

Hand at rest (no contraction or expansion)
Thumb expanded; others at rest ("positive" sign)
Index expanded; others at rest (#1 sign)
Index and middle fingers expanded; others contracted (#2 sign)
Index, middle, and ring fingers expanded; others contracted (#3 sign)
Index, middle, ring and baby fingers expanded; thumb contracted (#4 sign)
All fingers expanded (#5 sign)
All fingers contracted (fist)
Index and baby fingers out, others contracted (horn)
"Love and peace" sign Thus, the various embodiments described herein can enable a user, while wearing the wristband 115 as described herein, to make a variety of gestures. These gestures can be detected based on the wrist tendon and muscle movements detected by the sensor array 120 in the wristband 115.

Figure 12:
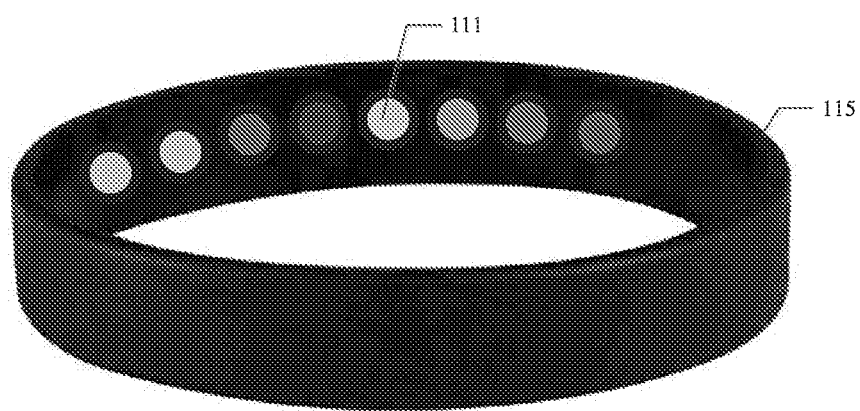
FIG. 12 illustrates an example embodiment of the placement of the sensor array on the posterior side of a wearable wristband.
Figure 13:
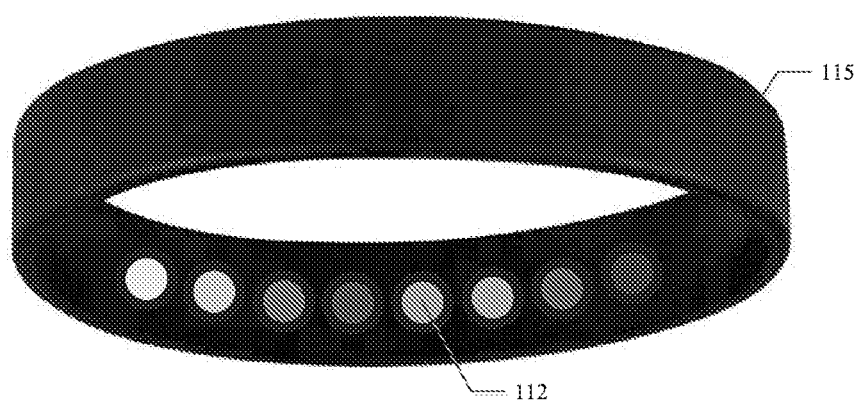
FIG. 13 illustrates an example embodiment of the placement of the sensor array on the anterior side of a wearable wristband.

FIG. 12 illustrates an example embodiment of the placement of the first sensor array portion 111 on the posterior side of a wearable wristband 115. FIG. 13 illustrates an example embodiment of the placement of the second sensor array portion 112 on the anterior side of a wearable wristband 115. As described above, the sensor portions 111 and 112 are brought into contact with the wrist of a user when the wristband 115 is worn. As the user makes a variety of gestures, the data corresponding to the particular gestures can be wirelessly transferred to a user interface of an external device. The external device can be separate from the wristband 115 or attached to the wristband as shown in FIG. 14.

Figure 14:
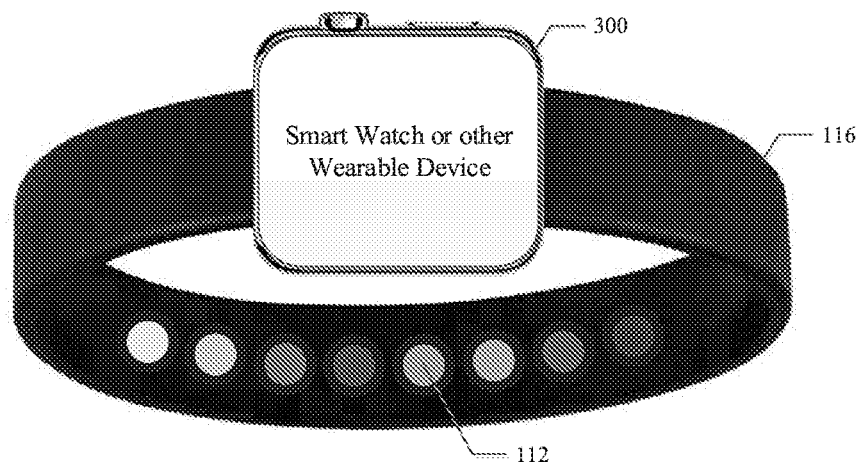
FIG. 14 illustrates an example embodiment of the placement of the sensor array on the anterior side of a wearable wristband integrated with a standard smart watch or other wearable device.

FIG. 14 illustrates another example embodiment of the placement of the second sensor array portion 112 on the anterior side of a wearable wristband 116. The first sensor array portion 111 on the posterior side of the wearable wristband 116 is present on the wristband 116, but not visible in FIG. 14. In the example embodiment of FIG. 14, the wristband 116 is integrated with or connected to a standard smart watch or other wearable device 300. In this example embodiment, the wearable device 300 can represent the external device to which the data corresponding to the particular gestures can be wirelessly transferred from the controller unit 120 and the sensor array 110 integrated into wristband 116. Given the gesture data received from the controller unit 120 and the sensor array 110, a user interface in the wearable device 300 can be controlled by the gestures made by the user and detected by the wristband 116. This configuration provided by the various embodiments described herein allows a user to control a wearable device 300 with one hand. Additionally, the various embodiments described herein allow a user to control a wearable device 300 without having to wear or carry a band or device separately from the wearable device 300. The various embodiments enable a user to wear a single device with sensors integrated into the wristband of the device and to control the device with wrist or finger gestures. In a similar manner, an external device not integrated with or connected to the wristband 116 can wirelessly receive gesture data from the controller unit 120 and the sensor array 110 and use the gesture data to control a user interface in the external device.

Referring now to FIG. 15, a processing flow diagram illustrates an example embodiment of a method 1100 as described herein. The method 1100 of an example embodiment includes: providing a sensor array integrated into a wristband, the sensor array including a plurality of pressure sensors positioned for contact with particular locations on a wrist of a user wearing the wristband (processing block 1110); providing a controller unit, the controller unit including a communication interface (processing block 1120); receiving a plurality of sensor signals generated by the sensor array, the plurality of sensor signals corresponding to movement detected at particular locations on the wrist of the user (processing block 1130); converting the plurality of sensor signals to a digital representation (processing block 1140); generating a composite data packet by combining the plurality of converted sensor signals into a composite digital value (processing block 1150); and providing the composite digital value to a processing unit of a wearable device for use in control of a user interface in the wearable device (processing block 1160).

Thus, a system and method to collect gesture input through wrist tendon and muscle sensing are disclosed. The various embodiments described herein and the usage of a gesture interface incorporated into the smart watch wristband can be applied to an enormous number of usage applications, such as user authentication or identification mechanisms, gaming, signal language interpretation (e.g., conversion to text/voice), etc. It will be apparent to those of ordinary skill in the art in view of the disclosure herein that the described embodiments can enable and provide an effective user interface for these and other applications.

Embodiments described herein are applicable for use with all types of semiconductor integrated circuit ("IC") chips. Examples of these IC chips include but are not limited to processors, controllers, chipset components, programmable logic arrays (PLAs), memory chips, network chips, systems on chip (SoCs), SSD/NAND controller ASICs, and the like. In addition, in some of the drawings, signal conductor lines are represented with lines. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments are not limited to the same. As manufacturing techniques (e.g., photolithography) mature over time, it is expected that devices of smaller size can be manufactured. In addition, well-known power/ground connections to integrated circuit (IC) chips and other components may or may not be shown within the figures, for simplicity of illustration and discussion, and so as not to obscure certain aspects of the embodiments. Further, arrangements may be shown in block diagram form in order to avoid obscuring embodiments, and also in view of the fact that specifics with respect to implementation of such block diagram arrangements are highly dependent upon the platform within which the embodiment is to be implemented, i.e., such specifics should be well within purview of one of ordinary skill in the art. Where specific details (e.g., circuits) are set forth in order to describe example embodiments, it should be apparent to one of ordinary skill in the art that embodiments can be practiced without, or with variation of, these specific details. The description is thus to be regarded as illustrative instead of limiting.

The term "coupled" may be used herein to refer to any type of relationship, direct or indirect, between the components in question, and may apply to electrical, mechanical, fluid, optical, electromagnetic, electromechanical or other connections. In addition, the terms "first", "second", etc. may be used herein only to facilitate discussion, and carry no particular temporal or chronological significance unless otherwise indicated.

Controller unit 120 may include one or more wireless transceivers, in some embodiments. Each of the wireless transceivers may be implemented as physical wireless adapters or virtual wireless adapters, sometimes referred to as "hardware radios" and "software radios," respectively. A single physical wireless adapter may be virtualized (e.g., using software) into multiple virtual wireless adapters. A physical wireless adapter typically connects to a hardware-based wireless access point. A virtual wireless adapter typically connects to a software-based wireless access point, sometimes referred to as a "SoftAP." For instance, a virtual wireless adapter may allow ad hoc communications between peer devices, such as a smartphone and a desktop computer or notebook computer. Various embodiments may use a single physical wireless adapter implemented as multiple virtual wireless adapters, multiple physical wireless adapters, multiple physical wireless adapters each implemented as multiple virtual wireless adapters, or some combination thereof. The example embodiments described herein are not limited in this respect.

The wireless transceivers may include or implement various communication techniques to allow the controller unit 120 to communicate with other electronic devices. For instance, the wireless transceivers may implement various types of standard communication elements designed to be interoperable with a network, such as one or more communications interfaces, network interfaces, network interface cards (NIC), radios, wireless transmitters/receivers (transceivers), wired and/or wireless communication media, physical connectors, and so forth.

By way of example, and not limitation, communication media includes wired communications media and wireless communications media. Examples of wired communications media may include a wire, cable, metal leads, printed circuit boards (PCB), backplanes, switch fabrics, semiconductor material, twisted-pair wire, co-axial cable, fiber optics, a propagated signal, and so forth. Examples of wireless communications media may include acoustic, radio-frequency (RF) spectrum, light (e.g., infrared and other parts of the spectrum), and other wireless media. Other embodiments can also use Li-Fi (Light Fidelity), which is a bidirectional, high speed and fully networked wireless optical communication technology similar to WiFi.

In various embodiments, the controller unit 120 may implement different types of wireless transceivers. Each of the wireless transceivers may implement or utilize a same or different set of communication parameters to communicate information between various electronic devices. In one embodiment, for example, each of the wireless transceivers may implement or utilize a different set of communication parameters to communicate information between controller unit 120 and any number of other devices. Some examples of communication parameters may include without limitation a communication protocol, a communication standard, a radio-frequency (RF) band, a radio, a transmitter/receiver (transceiver), a radio processor, a baseband processor, a network scanning threshold parameter, a radio-frequency channel parameter, an access point parameter, a rate selection parameter, a frame size parameter, an aggregation size parameter, a packet retry limit parameter, a protocol parameter, a radio parameter, modulation and coding scheme (MCS), acknowledgement parameter, media access control (MAC) layer parameter, physical (PHY) layer parameter, and any other communication parameters affecting operations for the wireless transceivers. The example embodiments described herein are not limited in this respect.

In various embodiments, the wireless transceivers may implement different communication parameters offering varying bandwidths, communications speeds, or transmission ranges. For instance, a first wireless transceiver may include a short-range interface implementing suitable communication parameters for shorter range communication of information, while a second wireless transceiver may include a long-range interface implementing suitable communication parameters for longer range communication of information.

In various embodiments, the terms "short-range" and "long-range" may be relative terms referring to associated communications ranges (or distances) for associated wireless transceivers as compared to each other rather than an objective standard. In one embodiment, for example, the term "short-range" may refer to a communications range or distance for the first wireless transceiver that is shorter than a communications range or distance for another wireless transceiver implemented for controller unit 120, such as a second wireless transceiver. Similarly, the term "long-range" may refer to a communications range or distance for the second wireless transceiver that is longer than a communications range or distance for another wireless transceiver implemented for the controller unit 120, such as the first wireless transceiver. The example embodiments described herein are not limited in this respect.

In one embodiment, for example, the wireless transceiver may include a radio designed to communicate information over a wireless personal area network (WPAN) or a wireless local area network (WLAN). The wireless transceiver may be arranged to provide data communications functionality in accordance with different types of lower range wireless network systems or protocols. Examples of suitable WPAN systems offering lower range data communication services may include a Bluetooth™ system as defined by the Bluetooth Special Interest Group, an infra-red (IR) system, an Institute of Electrical and Electronics Engineers (IEEE™) 802.15 system, a DASH7 system, wireless universal serial bus (USB), wireless high-definition (HD), an ultra-side band (UWB) system, and similar systems. Examples of suitable WLAN systems offering lower range data communications services may include the IEEE 802.xx series of protocols, such as the IEEE 802.11a/b/g/n series of standard protocols and variants (also referred to as "WiFi"). Other embodiments can also use Li-Fi (Light Fidelity), which is a bidirectional, high speed and fully networked wireless optical communication technology similar to WiFi. It may be appreciated that other wireless techniques may be implemented. The example embodiments described herein are not limited in this respect. In one embodiment, for example, the wireless transceiver may include a radio designed to communicate information over a wireless metropolitan area network (WMAN), a wireless wide area network (WWAN), or a cellular radiotelephone system. Another wireless transceiver may be arranged to provide data communications functionality in accordance with different types of longer range wireless network systems or protocols. Examples of suitable wireless network systems offering longer range data communication services may include the IEEE 802.xx series of protocols, such as the IEEE 802.11a/b/g/n series of standard protocols and variants, the IEEE 802.16 series of standard protocols and variants, the IEEE 802.20 series of standard protocols and variants (also referred to as "Mobile Broadband Wireless Access"), and so forth. Alternatively, the wireless transceiver may include a radio designed to communicate information across data networking links provided by one or more cellular radiotelephone systems. Examples of cellular radiotelephone systems offering data communications services may include GSM with General Packet Radio Service (GPRS) systems (GSM/GPRS), CDMA/1× RTT systems, Enhanced Data Rates for Global Evolution (EDGE) systems, Evolution Data Only or Evolution Data Optimized (EV-DO) systems, Evolution For Data and Voice (EV-DV) systems, High Speed Downlink Packet Access (HSDPA) systems, High Speed Uplink Packet Access (HSUPA), and similar systems. It may be appreciated that other wireless techniques may be implemented. The example embodiments described herein are not limited in this respect.

Although not shown, controller unit 120 may further include one or more device resources commonly implemented for electronic devices, such as various computing and communications platform hardware and software components typically implemented by a personal electronic device. Some examples of device resources may include without limitation a co-processor, a graphics processing unit (GPU), a chipset/platform control logic, an input/output (I/O) device, computer-readable media, network interfaces, portable power supplies (e.g., a battery), application programs, system programs, and so forth. The example embodiments described herein are not limited in this respect.

Included herein is a set of logic flows representative of example methodologies for performing novel aspects of the disclosed architecture. While, for purposes of simplicity of explanation, the one or more methodologies shown herein are shown and described as a series of acts, those of ordinary skill in the art will understand and appreciate that the methodologies are not limited by the order of acts. Some acts may, in accordance therewith, occur in a different order and/or concurrently with other acts from those shown and described herein. For example, those of ordinary skill in the art will understand and appreciate that a methodology can alternatively be represented as a series of interrelated states or events, such as in a state diagram. Moreover, not all acts illustrated in a methodology may be required for a novel implementation. A logic flow may be implemented in software, firmware, and/or hardware. In software and firmware embodiments, a logic flow may be implemented by computer executable instructions stored on at least one non-transitory computer readable medium or machine readable medium, such as an optical, magnetic or semiconductor storage. The example embodiments disclosed herein are not limited in this respect.

The various elements of the example embodiments as previously described with reference to the figures may include various hardware elements, software elements, or a combination of both. Examples of hardware elements may include devices, logic devices, components, processors, microprocessors, circuits, processors, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. However, determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints, as desired for a given implementation.

The example embodiments described herein provide a technical solution to a technical problem. The various embodiments improve the functioning of the electronic device and the related system by providing a system and method to collect gesture input through wrist tendon and muscle sensing. The various embodiments also serve to transform the state of various system components based on a dynamically determined system context. Additionally, the various embodiments effect an improvement in a variety of technical fields including the fields of dynamic data processing, electronic systems, mobile devices, wearable devices, Internet of Things (IoT) devices, data sensing systems, human/machine interfaces, gesture sensing, mobile computing, information sharing, and mobile communications.

Figure 16:
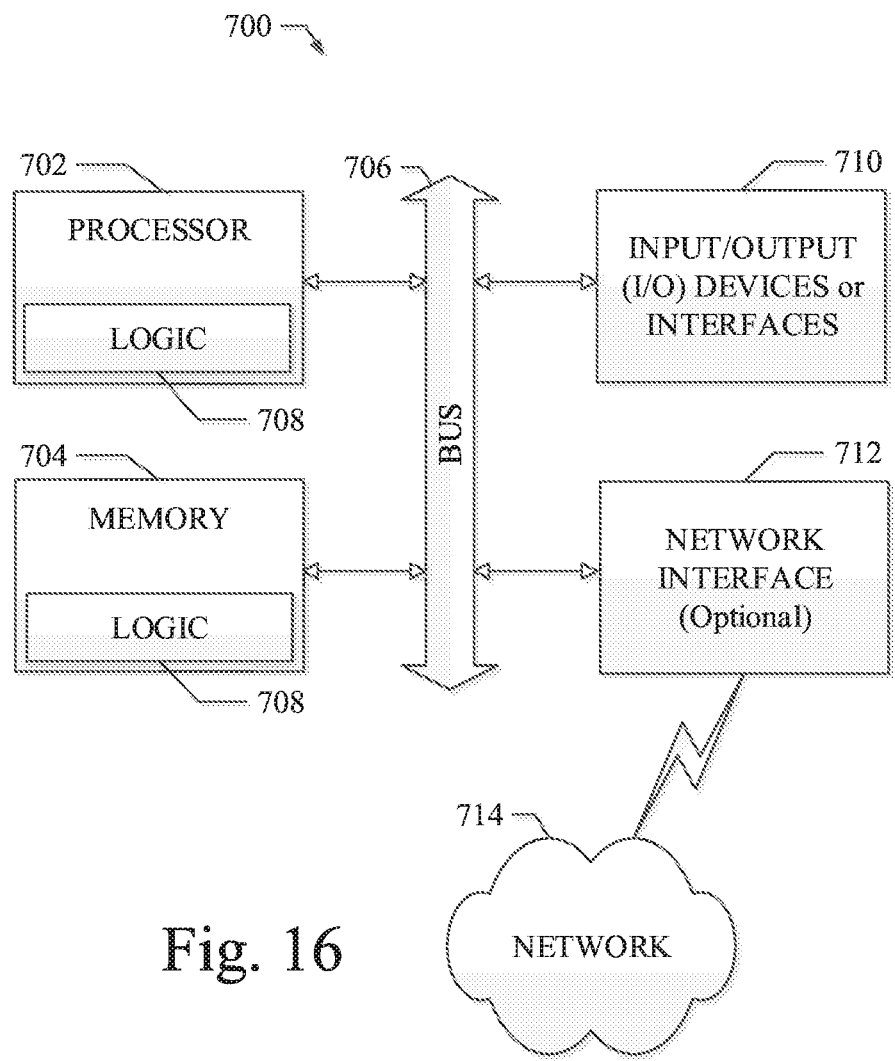
FIG. 16 shows a diagrammatic representation of a machine in the example form of a mobile computing and/or communication system within which a set of instructions when executed and/or processing logic when activated may cause the machine to perform any one or more of the methodologies described and/or claimed herein.

FIG. 16 shows a diagrammatic representation of a machine in the example form of an electronic device, such as a mobile computing and/or communication system 700 within which a set of instructions when executed and/or processing logic when activated may cause the machine to perform any one or more of the methodologies described and/or claimed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a laptop computer, a tablet computing system, a Personal Digital Assistant (PDA), a cellular telephone, a smartphone, a web appliance, a set-top box (STB), a network router, switch or bridge, or any machine capable of executing a set of instructions (sequential or otherwise) or activating processing logic that specify actions to be taken by that machine. Further, while only a single machine is illustrated, the term "machine" can also be taken to include any collection of machines that individually or jointly execute a set (or multiple sets) of instructions or processing logic to perform any one or more of the methodologies described and/or claimed herein.

The example mobile computing and/or communication system 700 includes a data processor 702 (e.g., a System-on-a-Chip [SoC], general processing core, graphics core, and optionally other processing logic) and a memory 704, which can communicate with each other via a bus or other data transfer system 706. The mobile computing and/or communication system 700 may further include various input/output (I/O) devices and/or interfaces 710, such as a touchscreen display and optionally a network interface 712. In an example embodiment, the optional network interface 712 can include one or more radio transceivers configured for compatibility with any one or more standard wireless and/or cellular protocols or access technologies (e.g., 2nd (2G), 2.5, 3rd (3G), 4th (4G) generation, and future generation radio access for cellular systems, Global System for Mobile communication (GSM), General Packet Radio Services (GPRS), Enhanced Data GSM Environment (EDGE), Wideband Code Division Multiple Access (WCDMA), LTE, CDMA2000, WLAN, Wireless Router (WR) mesh, and the like). Network interface 712 may also be configured for use with various other wired and/or wireless communication protocols, including TCP/IP, UDP, SIP, SMS, RTP, WAP, CDMA, TDMA, UMTS, UWB, WiFi, WiMax, Bluetooth™, IEEE™ 802.11x, and the like. Other embodiments can also use Li-Fi (Light Fidelity), which is a bidirectional, high speed and fully networked wireless optical communication technology similar to WiFi. In essence, network interface 712 may include or support virtually any wired and/or wireless communication mechanisms by which information may travel between the mobile computing and/or communication system 700 and another computing or communication system via network 714.

The memory 704 can represent a machine-readable medium on which is stored one or more sets of instructions, software, firmware, or other processing logic (e.g., logic 708) embodying any one or more of the methodologies or functions described and/or claimed herein. The logic 708, or a portion thereof, may also reside, completely or at least partially within the processor 702 during execution thereof by the mobile computing and/or communication system 700. As such, the memory 704 and the processor 702 may also constitute machine-readable media. The logic 708, or a portion thereof, may also be configured as processing logic or logic, at least a portion of which is partially implemented in hardware. The logic 708, or a portion thereof, may further be transmitted or received over a network 714 via the network interface 712. While the machine-readable medium of an example embodiment can be a single medium, the term "machine-readable medium" should be taken to include a single non-transitory medium or multiple non-transitory media (e.g., a centralized or distributed database, and/or associated caches and computing systems) that store the one or more sets of instructions. The term "machine-readable medium" can also be taken to include any non-transitory medium that is capable of storing, encoding or carrying a set of instructions for execution by the machine and that cause the machine to perform any one or more of the methodologies of the various embodiments, or that is capable of storing, encoding or carrying data structures utilized by or associated with such a set of instructions. The term "machine-readable medium" can accordingly be taken to include, but not be limited to, solid-state memories, optical media, and magnetic media.

With general reference to notations and nomenclature used herein, the description presented herein may be disclosed in terms of program procedures executed on a computer or a network of computers. These procedural descriptions and representations may be used by those of ordinary skill in the art to convey their work to others of ordinary skill in the art.

A procedure is generally conceived to be a self-consistent sequence of operations performed on electrical, magnetic, or optical signals capable of being stored, transferred, combined, compared, and otherwise manipulated. These signals may be referred to as bits, values, elements, symbols, characters, terms, numbers, or the like. It should be noted, however, that all of these and similar terms are to be associated with the appropriate physical quantities and are merely convenient labels applied to those quantities. Further, the manipulations performed are often referred to in terms such as adding or comparing, which operations may be executed by one or more machines. Useful machines for performing operations of various embodiments may include general-purpose digital computers or similar devices. Various embodiments also relate to apparatus or systems for performing these operations. This apparatus may be specially constructed for a purpose, or it may include a general-purpose computer as selectively activated or reconfigured by a computer program stored in the computer. The procedures presented herein are not inherently related to a particular computer or other apparatus. Various general-purpose machines may be used with programs written in accordance with teachings herein, or it may prove convenient to construct more specialized apparatus to perform methods described herein.

In various embodiments as described herein, example embodiments include at least the following examples.

An apparatus comprising: a sensor array integrated into a wristband, the sensor array including a plurality of pressure sensors positioned for contact with particular locations on a wrist of a user wearing the wristband; and a controller unit, the controller unit including a communication interface, the controller unit being configured to: receive a plurality of sensor signals generated by the sensor array, the plurality of sensor signals corresponding to movement detected at particular locations on the wrist of the user; convert the plurality of sensor signals to a digital representation; generate a composite data packet by combining the plurality of converted sensor signals into a composite digital value; and provide the composite digital value to a processing unit of a wearable device for use in control of a user interface in the wearable device. The apparatus as claimed above wherein the sensor array includes a first sensor array portion positioned on the posterior of the wrist of the user, the sensor array including a second sensor array portion positioned on the anterior of the wrist of the user.

The apparatus as claimed above further comprising a power source to provide power to the controller unit, wherein the power source is of a type from the group consisting of: a battery, a solar cell, an energy harvesting system, and a motion generator.

The apparatus as claimed above wherein the wearable device is attached to the wristband. The apparatus as claimed above wherein the wearable device is a smart watch or any other type of wearable device.

The apparatus as claimed above wherein the digital representation of each of the plurality of sensor signals is an eight bit value.

The apparatus as claimed above being further configured to forward the composite digital value to the processing unit of the wearable device via a data transfer mechanism of a type from the group consisting of: a wireless data transmission and a wired data transfer mechanism.

A method comprising: providing a sensor array integrated into a wristband, the sensor array including a plurality of pressure sensors positioned for contact with particular locations on a wrist of a user wearing the wristband; providing a controller unit, the controller unit including a communication interface; receiving a plurality of sensor signals generated by the sensor array, the plurality of sensor signals corresponding to movement detected at particular locations on the wrist of the user; converting the plurality of sensor signals to a digital representation; generating a composite data packet by combining the plurality of converted sensor signals into a composite digital value; and providing the composite digital value to a processing unit of a wearable device for use in control of a user interface in the wearable device.

The method as claimed above wherein the sensor array includes a first sensor array portion positioned on the posterior of the wrist of the user, the sensor array including a second sensor array portion positioned on the anterior of the wrist of the user.

The method as claimed above including providing a power source to provide power to the controller unit, wherein the power source is of a type from the group consisting of: a battery, a solar cell, an energy harvesting system, and a motion generator.

The method as claimed above wherein the wearable device is attached to the wristband.

The method as claimed above wherein the wearable device is a smart watch or any other wearable device.

The method as claimed above wherein the digital representation of each of the plurality of sensor signals is an eight bit value.

The method as claimed above including forwarding the composite digital value to the processing unit of the wearable device via a data transfer mechanism of a type from the group consisting of: a wireless data transmission and a wired data transfer mechanism.

A system comprising: a wearable device including a processing unit for use in control of a user interface in the wearable device; a sensor array integrated into a wristband, the sensor array including a plurality of pressure sensors positioned for contact with particular locations on a wrist of a user wearing the wristband; and a controller unit, the controller unit including a communication interface, the controller unit being configured to: receive a plurality of sensor signals generated by the sensor array, the plurality of sensor signals corresponding to movement detected at particular locations on the wrist of the user; convert the plurality of sensor signals to a digital representation; generate a composite data packet by combining the plurality of converted sensor signals into a composite digital value; and provide the composite digital value to the processing unit of the wearable device for use in control of the user interface in the wearable device.

The system as claimed above wherein the sensor array includes a first sensor array portion positioned on the posterior of the wrist of the user, the sensor array including a second sensor array portion positioned on the anterior of the wrist of the user.

The system as claimed above further comprising a power source to provide power to the controller unit, wherein the power source is of a type from the group consisting of: a battery, a solar cell, an energy harvesting system, and a motion generator.

The system as claimed above wherein the wearable device is attached to the wristband.

The system as claimed above wherein the wearable device is a smart watch or any other type of wearable device.

The system as claimed above wherein the digital representation of each of the plurality of sensor signals is an eight bit value.

The system as claimed above being further configured to forward the composite digital value to the processing unit of the wearable device via a data transfer mechanism of a type from the group consisting of: a wireless data transmission and a wired data transfer mechanism.

A non-transitory machine-useable storage medium embodying instructions which, when executed by a machine, cause the machine to: interface with a sensor array integrated into a wristband, the sensor array including a plurality of pressure sensors positioned for contact with particular locations on a wrist of a user wearing the wristband; interface with controller unit, the controller unit including a communication interface; receive a plurality of sensor signals generated by the sensor array, the plurality of sensor signals corresponding to movement detected at particular locations on the wrist of the user; convert the plurality of sensor signals to a digital representation; generate a composite data packet by combining the plurality of converted sensor signals into a composite digital value; and provide the composite digital value to a processing unit of a wearable device for use in control of a user interface in the wearable device.

The machine-useable storage medium as claimed above wherein the sensor array includes a first sensor array portion positioned on the posterior of the wrist of the user, the sensor array including a second sensor array portion positioned on the anterior of the wrist of the user.

The machine-useable storage medium as claimed above further comprising a power source to provide power to the controller unit, wherein the power source is of a type from the group consisting of: a battery, a solar cell, an energy harvesting system, and a motion generator.

The machine-useable storage medium as claimed above wherein the wearable device is attached to the wristband.

The machine-useable storage medium as claimed above wherein the wearable device is a smart watch or any other wearable device.

The machine-useable storage medium as claimed above wherein the digital representation of each of the plurality of sensor signals is an eight bit value.

The machine-useable storage medium as claimed above being further configured to forward the composite digital value to the processing unit of the wearable device via a data transfer mechanism of a type from the group consisting of: a wireless data transmission and a wired data transfer mechanism.

An apparatus comprising: a sensing means integrated into a wristband, the sensing means including a plurality of pressure sensors positioned for contact with particular locations on a wrist of a user wearing the wristband; and a controlling means, the controlling means including a communication interface, the controlling means being configured to: receive a plurality of sensor signals generated by the sensing means, the plurality of sensor signals corresponding to movement detected at particular locations on the wrist of the user; convert the plurality of sensor signals to a digital representation; generate a composite data packet by combining the plurality of converted sensor signals into a composite digital value; and provide the composite digital value to a processing unit of a wearable device for use in control of a user interface in the wearable device.

The apparatus as claimed above wherein the sensing means includes a first sensing means portion positioned on the posterior of the wrist of the user, the sensing means including a second sensing means portion positioned on the anterior of the wrist of the user.

The apparatus as claimed above further comprising a power source to provide power to the controller unit, wherein the power source is of a type from the group consisting of: a battery, a solar cell, an energy harvesting system, and a motion generator.

The apparatus as claimed above wherein the wearable device is attached to the wristband.

The apparatus as claimed above wherein the wearable device is a smart watch or any other type of wearable device.

The apparatus as claimed above wherein the digital representation of each of the plurality of sensor signals is an eight bit value.

The apparatus as claimed above being further configured to forward the composite digital value to the processing unit of the wearable device via a data transfer mechanism of a type from the group consisting of: a wireless data transmission and a wired data transfer mechanism.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An apparatus comprising:
a wearable device including a user interface and a processor; and
a wristband coupled to the wearable device, the wristband having an inner surface to face a wrist of a user wearing the wristband, an outer surface opposite the inner surface, a first annular edge, and a second annular edge opposite the first annular edge, the wristband including:
a sensor array including a plurality of pressure sensors positioned along the inner surface to contact particular locations on the wrist of the user wearing the wristband, the pressure sensors arranged such that a first set of the pressure sensors is positioned closer to the first annular edge than a second set of the pressure sensors, and the second set of the pressure sensors is positioned closer to the second annular edge than the first set of the pressure sensors, the pressure sensors of the first set of the pressure sensors are interleaved with the pressure sensors of the second set of the pressure sensors; and
a controller including a communication interface, the controller to:
convert a plurality of sensor signals corresponding to pressure levels detected at the particular locations on the wrist of the user to respective digital representations of the pressure levels, the plurality of sensor signals generated by the sensor array;
combine the digital representations of the pressure levels into a composite data packet; and
provide the composite data packet to the processor of the wearable device to control the user interface of the wearable device.

2. The apparatus of claim 1, wherein, in the composite data packet, the digital representations are arranged in order of a physical arrangement of the plurality of pressure sensors around the wrist of the user wearing the wristband, the sensor array including a first sensor array portion to be positioned on a posterior of the wrist of the user and a second sensor array portion to be positioned on an anterior of the wrist of the user, a first portion of the composite data packet including the digital representations corresponding to the first sensor array portion in order of the physical arrangement of the pressure sensors in the first sensor array portion, and a second portion of the composite data packet including the digital representations corresponding to the second sensor array portion in order of the physical arrangement of the pressure sensors in the second sensor array portion.

3. The apparatus of claim 1, further including a first power source to provide power to the controller, the wearable device including a second power source to provide power to the processor.

4. The apparatus of claim 1, wherein the wearable device is a smart watch.

5. The apparatus of claim 1, wherein each of the digital representations is an eight bit value.

6. The apparatus of claim 1, wherein the communication interface of the controller is to provide the composite data packet to the processor of the wearable device via a wireless data transmission.

7. The apparatus of claim 1, wherein the communication interface of the controller is to provide the composite data packet to the processor of the wearable device via a wired data transmission.

8. The apparatus of claim 1, wherein output signals from the plurality of pressure sensors are transferred to the controller through respective pull down resistors.

9. A method comprising:
converting, by executing an instruction with a first processor, a plurality of sensor signals generated by a sensor array to respective digital representations, the first processor and the sensor array integrated into a wristband, the wristband having an inner surface to face a wrist of a user wearing the wristband, an outer surface opposite the inner surface, a first annular edge, and a second annular edge opposite the first annular edge, the sensor array including a plurality of pressure sensors positioned along the inner surface to contact distinct locations on the wrist of the user wearing the wristband, the pressure sensors arranged such that a first set of the pressure sensors is positioned closer to the first annular edge than a second set of the pressure sensors, and the second set of the pressure sensors is positioned closer to the second annular edge than the first set of the pressure sensors, the pressure sensors of the first set of the pressure sensors are interleaved with the pressure sensors of the second set of the pressure sensors, the plurality of sensor signals corresponding to pressure levels detected at the distinct locations on the wrist of the user, the first processor including a communication interface;
combining, by executing an instruction with the first processor, the digital representations of the pressure levels into a composite data packet; and
providing, by executing an instruction with the first processor, the composite data packet to a second processor of a wearable device carried by the wristband to control a user interface of the wearable device.

10. The method of claim 9, wherein, in the composite data packet, the digital representations are arranged in order corresponding to a physical arrangement of the plurality of pressure sensors on the wrist of the user wearing the wristband, wherein the converting of the plurality of sensors signals includes converting signals from a first sensor array portion positioned on a posterior of the wrist of the user and converting signals from a second sensor array portion positioned on an anterior of the wrist of the user, wherein a first portion of the composite data packet includes the digital representations corresponding to the first sensor array portion in order of the physical arrangement of the first sensor array portion, and wherein a second portion of the composite data packet includes the digital representations corresponding to the second sensor array portion in order of the physical arrangement of the second sensor array portion.

11. The method of claim 9, wherein each of the digital representations is an eight bit value.

12. The method of claim 9, wherein the providing of the composite data packet includes transmitting the composite data packet via at least one of a wireless data transmission or a wired data transmission.

13. A wearable device comprising:
a housing including a user interface and a processor to control the user interface;
a wristband having an inner surface to face a wrist of a user wearing the wristband, an outer surface opposite the inner surface, a first annular edge, and a second annular edge opposite the first annular edge, the housing coupled to the wristband;

a sensor array integrated into the wristband, the sensor array including a plurality of pressure sensors positioned along the inner surface to contact separate locations on the wrist of the user wearing the wristband, the pressure sensors arranged such that a first set of the pressure sensors is positioned closer to the first annular edge than a second set of the pressure sensors, and the second set of the pressure sensors is positioned closer to the second annular edge than the first set of the pressure sensors, the pressure sensors of the first set of the pressure sensors are interleaved with the pressure sensors of the second set of the pressure sensors; and a controller integrated into the wristband, the controller including a communication interface, the controller to:
convert a plurality of sensor signals corresponding to pressure levels detected at the locations on the wrist of the user to respective digital representations of the pressure levels, the plurality of sensor signals generated by the sensor array;
combine the digital representations of the pressure levels into a composite data packet; and
provide the composite data packet to the processor in the housing to control the user interface.

14. The wearable device of claim 13, wherein the digital representations in the composite data packet are arranged in order of a physical arrangement of the plurality of pressure sensors around the wristband, a first portion of the sensor array is to be positioned on a posterior of the wrist of the user and a second portion of the sensor array is to be positioned on an anterior of the wrist of the user, a first portion of the composite data packet includes the digital representations corresponding to the pressure sensors in the first portion of the sensor array in the order of the physical arrangement of the pressure sensors in the first portion of the sensor array, and a second portion of the composite data packet includes the digital representations corresponding to the pressure sensors in the second portion of the sensor array in the order of the physical arrangement of the pressure sensors in the second portion of the sensor array.

15. The wearable device of claim 13, further including a first power source integrated into the wristband, the first power source including at least one of a battery, a solar cell, an energy harvesting system, or a motion generator.

16. The wearable device of claim 15, wherein the housing includes a second power source.

17. The wearable device of claim 13, wherein the wearable device is a smart watch.

18. The wearable device of claim 13, wherein each of the digital representations of is an eight bit value.

19. The wearable device of claim 13, wherein the communication interface is to provide the composite data packet to the processor via at least one of a wireless data transmission or a wired data transmission.

* * * * *